United States Patent
Mcclintock

(10) Patent No.: US 10,905,484 B2
(45) Date of Patent: Feb. 2, 2021

(54) SURGICAL FIXATION ASSEMBLIES AND METHODS OF USE

(71) Applicant: K2M, Inc., Leesburg, VA (US)

(72) Inventor: Larry Mcclintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 114 days.

(21) Appl. No.: 15/999,658

(22) PCT Filed: Feb. 21, 2017

(86) PCT No.: PCT/US2017/018667
§ 371 (c)(1),
(2) Date: Aug. 20, 2018

(87) PCT Pub. No.: WO2017/143330
PCT Pub. Date: Aug. 24, 2017

(65) Prior Publication Data
US 2020/0085478 A1 Mar. 19, 2020

Related U.S. Application Data

(60) Provisional application No. 62/296,688, filed on Feb. 18, 2016.

(51) Int. Cl.
*A61B 17/70* (2006.01)
*A61B 17/86* (2006.01)
*A61B 17/88* (2006.01)

(52) U.S. Cl.
CPC ...... *A61B 17/8685* (2013.01); *A61B 17/7032* (2013.01); *A61B 17/7037* (2013.01);
(Continued)

(58) Field of Classification Search
CPC ............ A61B 17/8685; A61B 17/7032; A61B 17/7037; A61B 17/7059; A61B 17/8625;
(Continued)

(56) References Cited

U.S. PATENT DOCUMENTS 5,683,394 A * 11/1997 Rinner ................. A61F 2/4455
606/86 R
6,767,367 B1 * 7/2004 Michelson .............. A61F 2/447
623/17.16
(Continued)

FOREIGN PATENT DOCUMENTS

WO 0035361 A1 6/2000

OTHER PUBLICATIONS

International Search Report and Written Opinion issued in PCT/US17/18667 dated May 15, 2017.

*Primary Examiner* — Ellen C Hammond
*Assistant Examiner* — David C Comstock
(74) *Attorney, Agent, or Firm* — Lerner, David, Littenberg, Krumholz & Mentlik, LLP

(57) ABSTRACT

A fixation assembly includes an anchor, a cam, and a shaft. The anchor defines a longitudinal axis and includes a spine that extends along the longitudinal axis. The spine has a first projection and a second projection that extend from the spine in a direction transverse to a longitudinal axis. The anchor defines a slot between the first and second projections. The cam is disposed with the slot and is positioned to rotate about the longitudinal axis between first and second positions to enable the first and second projections and the cam to secure the anchor to osseous tissue. The shaft is rotatably disposed within the anchor and positioned to rotate the cam between the first and second positions. In the first position, the cam is aligned with the first and second projections, and in the second position, the cam is misaligned with the first and second projections.

20 Claims, 8 Drawing Sheets

(52) U.S. Cl.
CPC ........ *A61B 17/7059* (2013.01); *A61B 17/864* (2013.01); *A61B 17/8625* (2013.01); *A61B 2017/8655* (2013.01)

(58) Field of Classification Search
CPC .............. A61B 17/864; A61B 17/8655; A61B 2017/8655; A61B 17/725; A61B 17/7258; A61B 17/7266; A61B 17/7275; A61B 17/844
USPC ....... 606/279, 266, 267, 268, 270, 272, 308, 606/310, 313, 326, 327
See application file for complete search history.

(56) References Cited

U.S. PATENT DOCUMENTS

| | | | |
|---|---|---|---|
| 7,594,932 B2* | 9/2009 | Aferzon | A61F 2/447 623/17.16 |
| 7,862,593 B2* | 1/2011 | Clement | A61B 17/7037 606/250 |
| 8,636,738 B2 | 1/2014 | McClintock et al. | |
| 8,814,919 B2 | 8/2014 | Barrus et al. | |
| 8,870,877 B2* | 10/2014 | Koogle, Jr. | A61F 2/0811 606/326 |
| 9,393,049 B2 | 7/2016 | Jones et al. | |
| 9,820,867 B2* | 11/2017 | Tepper | A61B 17/7059 |
| 2004/0158327 A1* | 8/2004 | Bagby | A61F 2/4611 623/17.11 |
| 2007/0293866 A1* | 12/2007 | Stoeckel | A61B 17/7266 606/326 |
| 2009/0125071 A1 | 5/2009 | Skinlo et al. | |
| 2010/0131019 A1* | 5/2010 | Lob | A61B 17/68 606/327 |
| 2010/0228301 A1 | 9/2010 | Greenhalgh et al. | |
| 2012/0123485 A1 | 5/2012 | Dehnad et al. | |
| 2012/0318605 A1 | 12/2012 | Palagi | |
| 2013/0261663 A1 | 10/2013 | Bittenson | |

* cited by examiner

SURGICAL FIXATION ASSEMBLIES AND METHODS OF USE

CROSS-REFERENCE TO RELATED APPLICATIONS

This application claims the benefit of U.S. Provisional Patent Application No. 62/296,688, filed Feb. 18, 2016, the entire disclosure of which is incorporated by reference herein.

TECHNICAL FIELD

This disclosure relates generally to spinal surgery. More specifically, the present disclosure relates to surgical fixation assemblies for spinal stabilization and methods of use.

BACKGROUND

The human spine is the supporting axis of the body and makes all the movements of a person's head, arms, and legs possible. It is a highly flexible structure, capable of a high degree of curvature and twist in nearly every direction. An adult spine generally has twenty-four vertebrae, which can be categorized into three major sections. These categories include the cervical spine, the thoracic spine, and the lumber spine. The cervical spine is composed of the upper seven vertebrae, the thoracic spine is composed of the next twelve vertebrae, and the lumber spine is composed of the final five vertebrae. Below the lumber spine is a bone called the sacrum, which is part of the pelvis. Muscles and ligaments are attached to a slender projection from the back of the vertebrae known as the spinous process. Housed within a narrow channel in the center of spine is the spinal cord. All the nerves of the body are connected to the spinal cord.

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

Depending upon how such systems are coupled to the spine, the systems may be classified as anterior, posterior, or lateral implants. For example, lateral and anterior systems are coupled to the anterior portion of the spine. Posterior systems generally comprise a pair of rods that are fixed to adjacent vertebrae with fixation assemblies, such as pedicle screws, on either side of the spinous process along a section of the spine. For example, several pedicle screws may be secured to a spine during a procedure and, depending upon the number of pedicle screws and the length of those pedicle screws, this process could be a very time and labor intensive part of the procedure. In particular, each pedicle screw would require several rotations before becoming fully secured into the spine.

SUMMARY

In one aspect, the present disclosure is directed to a fixation assembly that includes an anchor, a cam, and a shaft. The anchor defines a longitudinal axis and includes a spine that extends along the longitudinal axis. The spine has a first projection and a second projection that extend from the spine in a direction transverse to the longitudinal axis. The anchor defines a slot between the first and second projections. A cam is disposed within the slot of the anchor. The cam is positioned to rotate about the longitudinal axis of the anchor between a first position and a second position to enable the first and second projections and the cam to secure the anchor to osseous tissue. In the first position, the cam is aligned with the first and second projections. In the second position, the cam is misaligned with the first and second projections. The shaft is rotatably disposed within the anchor and positioned to rotate the cam between the first and second positions.

The anchor may include a connection assembly that extends proximally from the spine and is configured to support a housing assembly. The anchor may define an aperture therethrough that receives the shaft.

The fixation assembly may further include a cap that secures the shaft to the anchor. A flange may be supported on the anchor and configured to limit insertion depth of the anchor.

In certain embodiments, the connection assembly may include a head section and a neck section. The head section may be spherically formed.

In some embodiments, the connection assembly may include a threaded neck section configured to threadably receive a nut.

In embodiments, the cam may include an engagement surface configured to cut or thread into osseous tissue. The cam may define a bore therethrough that receives the shaft therein. The shaft may include one or more ridges that extend longitudinally along the shaft. The bore of the cam may be keyed to accommodate the one or more ridges such that the one or more ridges drive rotation of the cam as the shaft rotates about the longitudinal axis of the anchor.

According to one aspect of the present disclosure, a method for securing a fixation assembly to osseous tissue is provided. The method includes inserting an anchor into a hole in osseous tissue, rotating a shaft received in the anchor relative to the anchor to rotate a cam disposed in the anchor from a first position, in which the cam is aligned with a projection extending from the anchor, to second position, in which the cam is misaligned with the projection of the anchor to cause the projection and the cam to secure to osseous tissue surrounding the hole.

The method may include rotating the cam from the first position to the second position to rotate the cam up to about 180 degrees relative to the anchor. The method may include connecting a spinal rod to a housing assembly supported on a connection assembly of the anchor.

The method may involve rotating a cams disposed in the anchor from a first position, in which each cam is aligned with the projection extending from the anchor, to a second position, in which each cam is misaligned with the projection of the anchor to cause the projection and the cams to secure the anchor to osseous tissue surrounding the hole.

The method may include drilling the hole in osseous tissue.

According to yet another aspect of the present disclosure, a fixation system includes a housing assembly, an anchor, a cam, and a shaft. The anchor is received within the housing assembly. The anchor defines a longitudinal axis and includes a spine that extends along the longitudinal axis. The spine has a first projection and a second projection that extend from the spine in a direction transverse to the longitudinal axis. The anchor defines a slot between the first and second projections. A cam is received within the slot of the anchor. The cam is positioned to rotate about the longitudinal axis of the anchor between a first position and a second position to enable the first and second projections and the cam to secure the anchor to osseous tissue. In the first position, the cam is aligned with the first and second projections. In the second position, the cam is misaligned with the first and second projections. The shaft is rotatably received within the anchor and positioned to rotate the cam between the first and second positions.

In some embodiments, the anchor may include a connection assembly that extends proximally from the spine and supports the housing assembly thereon. The housing assembly may be polyaxially mounted on a head of the connection assembly. In embodiments, the housing assembly may have a taper lock arrangement. In some embodiments, the housing assembly may have a set screw type arrangement.

Other aspects, features, and advantages will be apparent from the description, the drawings, and the claims that follow.

BRIEF DESCRIPTION OF THE DRAWINGS

Various embodiments of the present disclosure are described herein below with reference to the drawings, wherein.

DETAILED DESCRIPTION

Figure 1A:
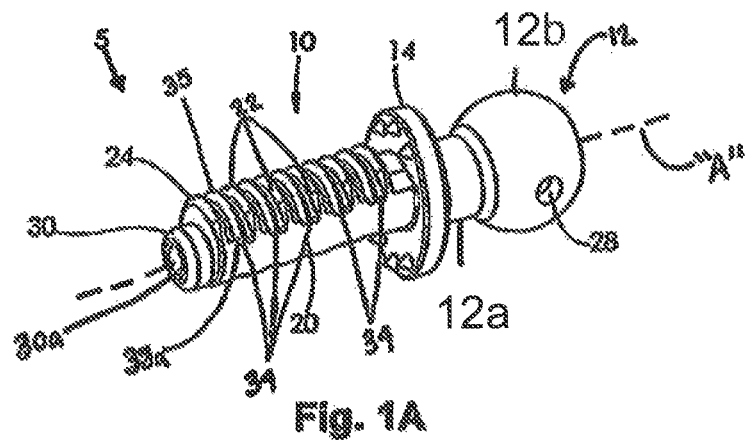
FIG. 1A is an isometric view of a fixation assembly in a first position according to an embodiment of the present disclosure.

Various embodiments will now be described in detail with reference to the drawings, wherein like reference numerals identify similar or identical elements. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. Further still, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

In general, the present disclosure relates to fixation systems including fixation and housing assemblies coupled together to facilitate spinal stabilization. The fixation assemblies of these fixation systems are securable to osseous tissue, for example, a pedicle of a vertebra, iliac of the pelvis, or the like, and are configured to reduce insertion time by limiting rotational effort required for insertion into such tissue.

Figure 1B:
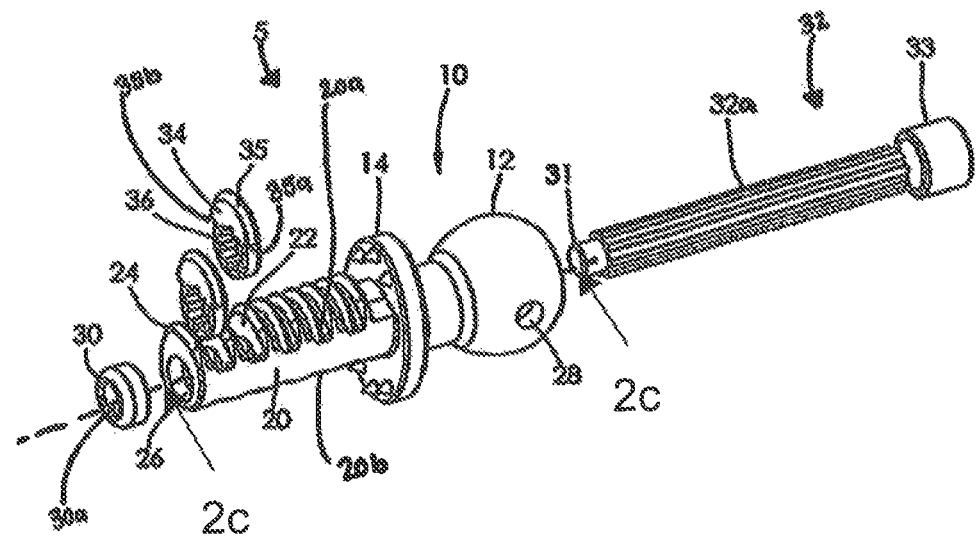
FIG. 1B is an isometric view, with parts separated, of the fixation assembly of FIG. 1A.

With reference to FIGS. 1A and 1B, an embodiment of a fixation assembly 5 includes an anchor assembly 10 defining a longitudinal axis "A" and a shaft 32. The shaft 32 of the fixation assembly 5 may include one or more ridges 32a that extend longitudinally along the shaft 32 so that the shaft 32 is in the form of a spline shaft. The ridges 32a may be positioned circumferentially about the shaft 32 at spaced-apart locations, which may be evenly and/or unevenly spaced. The ridges 32a, or portions thereof, may extend an entire or partial length of the shaft 32, and although shown as linear, can have any suitable configuration such as non-linear, interrupted, arcuate, etc., and/or combinations thereof. Further, although the ridges 32a are shown having a circular transverse cross-section, the ridges 32a, or portions thereof, may have any suitable cross-section including circular and non-circular configurations such as elliptical, rectangular, star, etc., and/or combinations thereof. As seen in FIG. 1B, the shaft 32 may include a tip 31 on a distal end portion and a drive sleeve 33 on a proximal end portion that defines a driving recess 33a (FIG. 3B) therein configured to receive a driving tool (not shown) such as a screw driver. The tip 31 may have an outer diameter smaller than an outer diameter of the shaft 32. The drive sleeve 33 may be an integral or monolithic part of the shaft 32. The drive sleeve 33 defines an outer diameter larger than an outer diameter defined by the shaft 32.

Figure 2A:
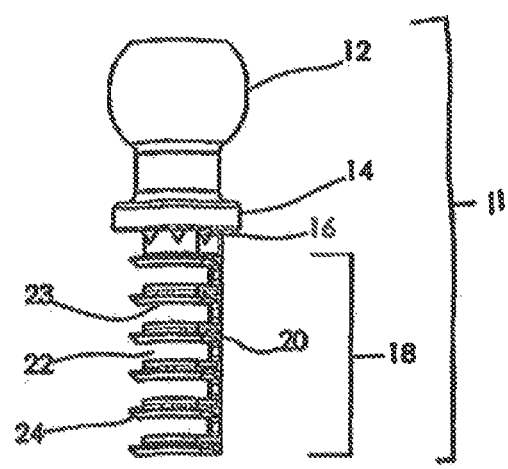
FIG. 2A is a front view of an anchor of an anchor assembly of the fixation assembly of FIGS. 1A and 1B.
Figure 2B:
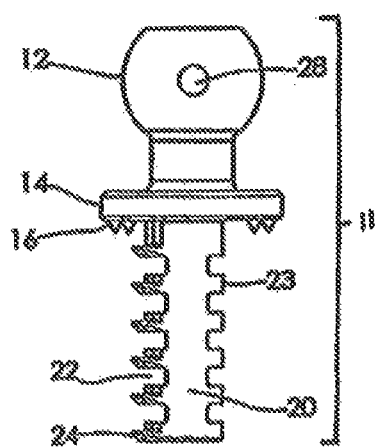
FIG. 2B is a side view of the anchor of the anchor assembly of FIG. 2A.

With continued reference to FIG. 1B, the anchor assembly 10 of the fixation assembly 5 generally includes a connection assembly 12, a flange 14, a spine 20, cams 34, and a cap 30. The connection assembly 12, the flange 14, and the spine 20 together define an anchor 11 of the anchor assembly 10 (FIGS. 2A and 2B). The anchor 11 may be integrally formed and/or monolithic (see FIGS. 2A-2C).

Figure 2C:
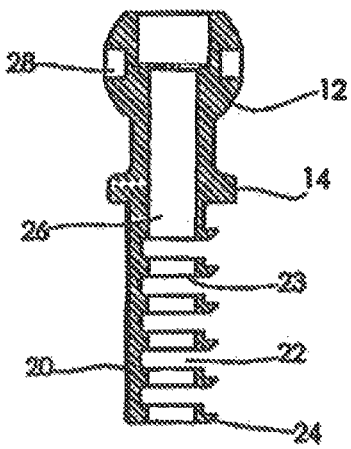
FIG. 2C is a cross-section of the anchor of the anchor assembly of FIG. 2A as taken along section line 2C-2C shown in FIG. 1B.
Figure 6A:
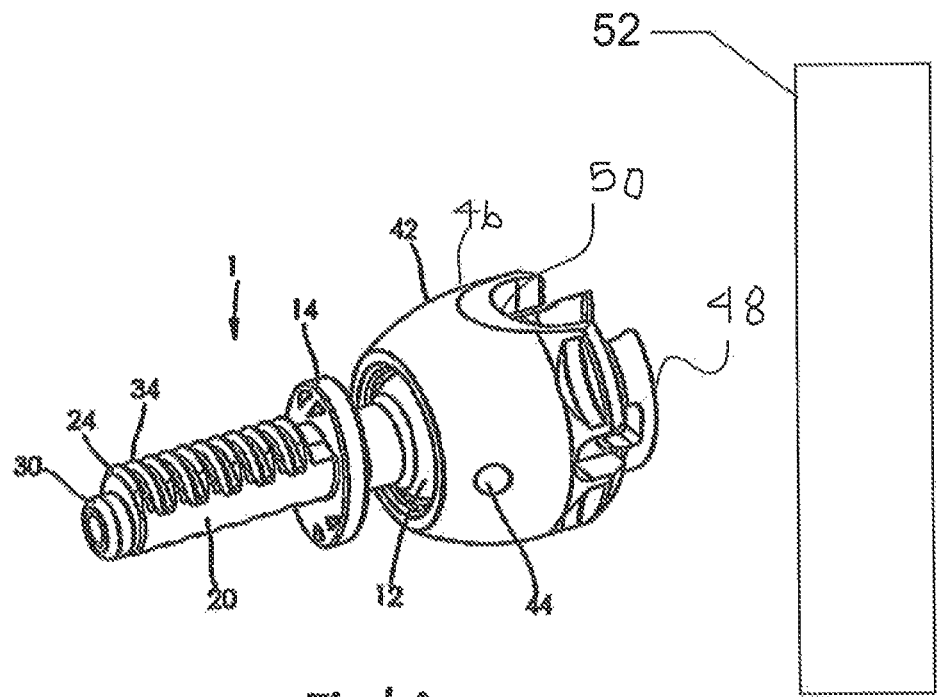
FIG. 6A is an isometric view of a fixation system and a spinal rod according to an embodiment of the present disclosure.
Figure 6B:
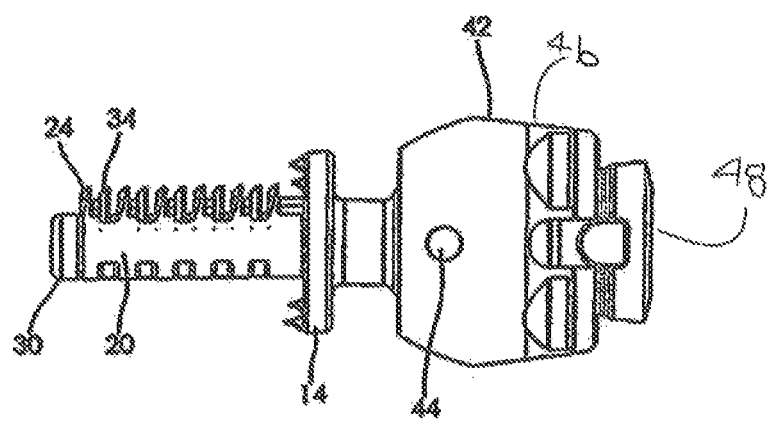
FIG. 6B is side view of the fixation system of FIG. 6A.

As seen in FIGS. 2A-2C, the connection assembly 12 of the anchor assembly 10 generally includes two components. The first component of the connection assembly 12, which is directly connected to the flange 14 of the anchor assembly 10, is a neck 12a. The neck 12a of the connection assembly 12 may be integrally formed with the flange 14 of the anchor assembly 10. The second component of the connection assembly 12 is a head 12b that extends from the neck 12a, and which may be integrally formed with the neck 12a. The head 12b is configured to facilitate attachment between the fixation assembly 5 and another surgical device, such as a housing assembly 42 (FIGS. 6A and 6B) to form a fixation system, for example. The head 12b has a spherical configuration configured to facilitate multi or polyaxial movement of the fixation assembly 5 relative to the housing assembly 42 when coupled thereto, for example. The head 12b of the connection assembly 12 defines a transverse bore 28 that extends transverse to the longitudinal axis "A" defined by the anchor assembly 10. The transverse bore 28 of the head 12b is configured to receive a pin 44 for mounting the housing assembly 42 to the fixation assembly 5 (FIGS. 6A and 6B).

With continued reference to FIGS. 2A-2C, the flange 14 of the anchor assembly 10 is positioned between the connection assembly 12 and the spine 20 of the anchor assembly 10 to separate the connection assembly 12 from the spine 20. The flange 14 functions as a guide to ensure proper placement of the fixation assembly 5, for example, by limiting insertion depth of the fixation assembly 5 when a distal surface of the flange 14 abuts against osseous tissue (e.g., full insertion depth).

Although the flange 14 of the anchor assembly 10 may have any suitable size and/or shape (e.g., circular or non-circular), the flange 14 may be larger than a targeted osseous tissue such as a pedicle. The flange 14 may be elliptical in shape (FIGS. 1A and 1B). The flange 14 may include one or more spikes 16 that extend distally from the distal surface of the flange 14 to facilitate tissue gripping. One or more spikes 16, which may have any suitable shape, configuration, and/or positioning on the distal surface of the flange 14. For example, one or more of the spikes 16 may be positioned radially outward from the longitudinal axis "A" and/or adjacent to an outer circumference of the flange 14. Such radially outward positioning of the spikes 16 provides increased counter torque, for instance, while the spikes 14 are engaged with tissue to inhibit the spine 20 from rotating as the shaft 32 rotates relative to the connection assembly 12. Two or more of the spikes 16 may be spaced apart evenly and/or unevenly. In some embodiments, the flange 14 may be devoid of spikes 16.

The spine 20 of the anchor assembly 10 extends distally from the flange 14 of the anchor assembly 10 along the longitudinal axis "A" of the anchor assembly 10, and defines a slotted area 18. The slotted area 18 of the spine 20 may extend the entire and/or partial length of the spine 20. One or more projections 23 extend outwardly from the spine 20 in a direction transverse to the longitudinal axis "A" of the anchor assembly 10 (e.g., perpendicular to longitudinal axis "A" and parallel to the flange 14). Each of the projections 23 may include an angled surface 24 configured to cut or thread into osseous tissue. Additionally, each of the projections 23 may include any suitable circular or non-circular shape such as elliptical ring, for example. In some embodiments, the shape and/or size of the projections 23 may vary relative to one another and/or relative to the flange 14. For example, as seen in FIG. 2c, the flange 14 may be wider than the projections 23.

A plurality of slots 22 is also defined in the slotted area 18 of the spine 20 of the anchor assembly 10. Each slot 22 of the spine 20 is defined adjacent projections 23 of the spine 20 and each slot 22 is configured to receive a respective one of the cams 34 of the anchor assembly 10. The number and/or arrangement of the projections 23, slots 22, and/or cams 34 can be increased or decreased as desired, for example, to change insertion depth, an amount of tissue purchase, and/or to accommodate patient anatomical differences.

With specific reference to FIG. 2C, an aperture 26 is defined through the connection assembly 12, the flange 14, and the projections 23 of the spine 20, and which is configured to receive the shaft 32 and the drive sleeve 33 of the anchor assembly 10 therein. The aperture 26 may be defined so that the longitudinal axis "A" of the anchor assembly 10 is centrally defined therethrough. The aperture 26 may have a larger diameter at a proximal end portion of the connection assembly 12 to accommodate the drive sleeve 33 of the shaft 32.

Referring to FIG. 1B, the cap 30 of the anchor assembly 10, which may be blunt, is configured to fit about the tip 31 of the shaft 32 to facilitate securement of the shaft 32 to the anchor assembly 10. The cap 30 defines a bore 30a that extends therethrough for receiving the tip 31 of the shaft 32. In some embodiments, the cap 30 may be closed at a distal end portion thereof such that the bore 30a only extends partially through the cap 30. The cap 30 may be secured to the shaft 32 of the anchor assembly 10 using any known securement technique such as fastening, welding, adhesive, threading, press-fit, etc.

Figure 3A:
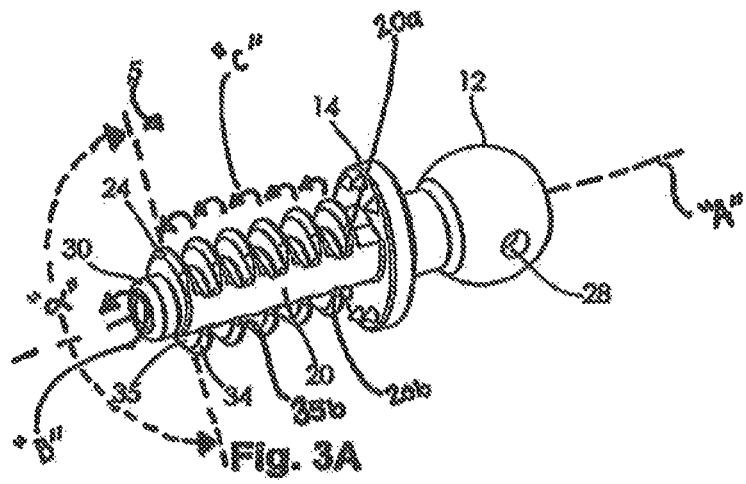
FIG. 3A is an isometric view of the fixation assembly of FIG. 1A in a second position.
Figure 3B:
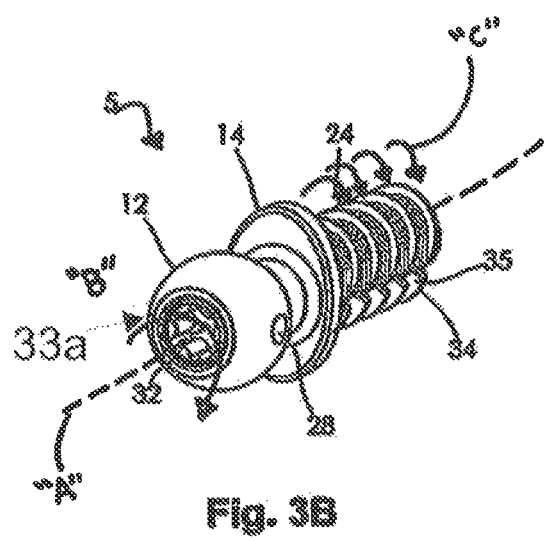
FIG. 3B is another isometric view of the fixation assembly of FIG. 3A.

As seen in FIGS. 1B, 3A, and 3B, each cam 34 is configured for insertion into the spine 20 of the anchor assembly 10 via a respective one of the slots 22 of the anchor assembly 10. Each cam 34 includes an engagement surface 35 having a first side 35a and a second side 35b. Engagement surface 35 may be angled similar to the angled surfaces 24 of the projections 23 of the spine 20 for cutting and/or threading into osseous tissue. Each cam 34 defines a bore 36 therethrough that is configured to accommodate the shaft 32 (e.g., keyed to the shaft 32 and ridges 32a of the shaft 32) such that the cams 34 are configured to rotate with the shaft 32 as the shaft 32 rotates relative to the spine 20.

In use, a hole can be drilled or otherwise formed into osseous tissue using known devices and techniques (e.g., punching, cutting, coring, etc.). While in an initial, undeployed position (see FIG. 1A), the fixation assembly 5 can then be inserted into the hole and advanced so that the spikes 16 of the flange 14 of the fixation assembly 5 are driven into osseous tissue surrounding the hole until the flange 14 abuts the osseous tissue (e.g., fully inserted). In the initial, undeployed position of the fixation assembly 5, the projections 23 of the spine 20 are aligned with the engagement surfaces 35 of the cams 34 and the first sides 35a of the engagement surfaces 35 of the cams 34 are engaged with the spine 20 on first side 20a thereof while the second sides 35b of the engagement surfaces 35 of the cams 34 are free.

As seen in FIGS. 3A and 3B, once the fixation assembly 5 is fully inserted into osseous tissue, the shaft 32 of the fixation assembly 5 can be rotated (e.g., via a driving tool such as a screw driver) about longitudinal axis "A," as indicated by arrow "B," such that the ridges 32a of the shaft 32 rotate the cams 34 of the fixation assembly 5 about the longitudinal axis "A" and relative to the projections 23 of the spine 20, as indicated by arrows "C." In particular, as shaft 32 rotates about longitudinal axis "A," it causes the cams 34 to rotate in the same direction so that the engagement surfaces 35 of the cams 34 move radially outward and away from the projections 23 of the spine 20. As the cams 34 rotate relative to the projections 23, the fixation assembly 5 transitions through a rotation angle "a," from the initial, undeployed position towards a deployed position (FIGS. 3A and 3B), so that the cams 34 cut or thread into the osseous tissue for securing the fixation assembly 5 to the osseous tissue (e.g., the cams 34 are frictionally engaged with the osseous tissue which inhibits reverse rotation of cams 34 towards the initial, undeployed position). In a fully deployed position, the projections 23 of the spine 20 are misaligned with the engagement surfaces 35 of the cams 34 and the second sides 35a of the engagement surfaces 35 of the cams 34 are engaged with the spine 20 on a second side 20b thereof while the first sides 35a of the engagement surfaces 35 of the cams 34 are free.

While the full rotation angle "a" of the cams 34 is illustrated as about 180 degrees, for example in FIGS. 3A and 3B, it may not be necessary to fully rotate the cams 34 to establish sufficient tissue purchase for securing the fixation assembly 5 to the osseous tissue. Rotation of the cams 34 can be performed incrementally, as desired.

Advantageously, securement of fixation assembly 5 is achieved with minimal rotational driving effort as compared to the multiple rotations required to distally advance and secure traditional pedicle screws. Also, the fixation assembly 5 may be shorter in length than a traditional bone screw and may be configured not to extend into predetermined portions of osseous tissue. For example, if the osseous tissue is a pedicle, then the fixation assembly 5 can have length that would not extend into the vertebral body interspace. Additionally, the fixation assembly 5, or portions thereof, may be comprised of any biocompatible material. Non-limiting examples of such biocompatible material includes titanium, titanium alloy, stainless steel, nickel titanium, cobalt chrome, and polyetheretherketone ("PEEK").

Figure 4A:
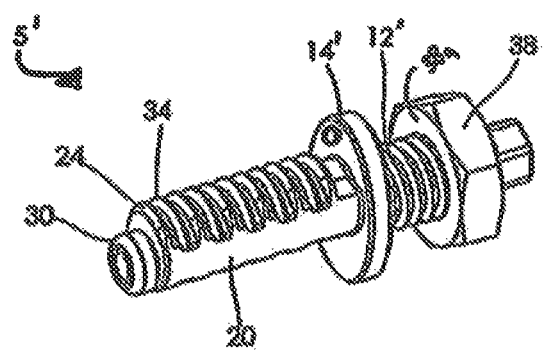
FIG. 4A is an isometric view of another embodiment of a fixation assembly in a first position according to the present disclosure.
Figure 4B:
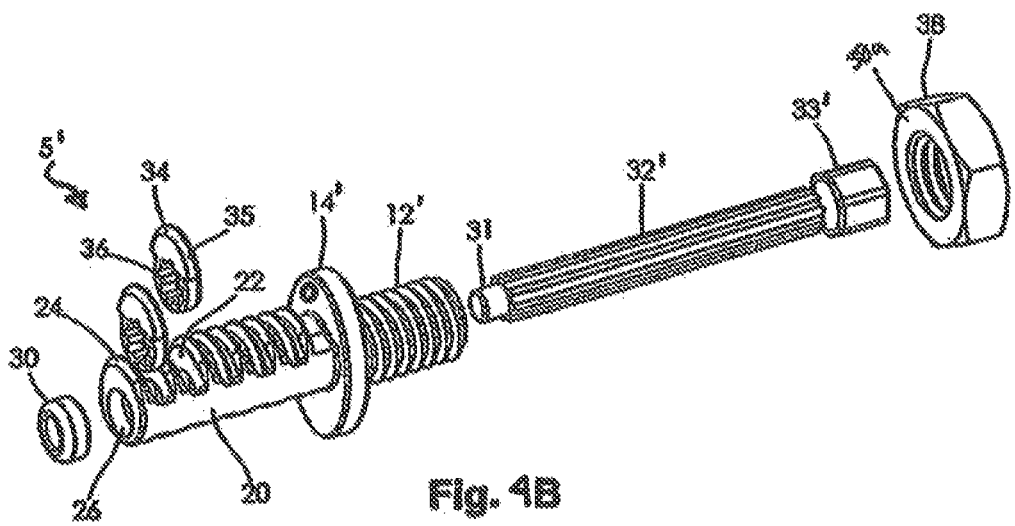
FIG. 4B is an isometric view, with parts separated, of the fixation assembly of FIG. 4A.
Figure 4C:
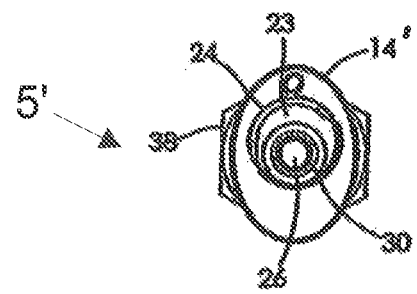
FIG. 4C is an end view of the fixation assembly of FIG. 4A.
Figure 5A:
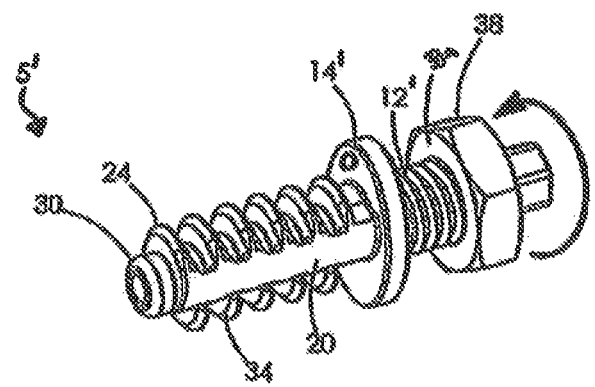
FIG. 5A is an isometric view of the fixation assembly of FIG. 4A in a second position.
Figure 5B:
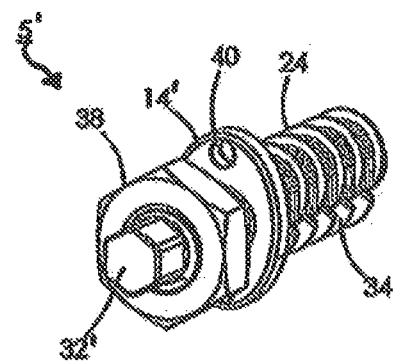
FIG. 5B is another isometric view of the fixation assembly of FIG. 5A.
Figure 5C:
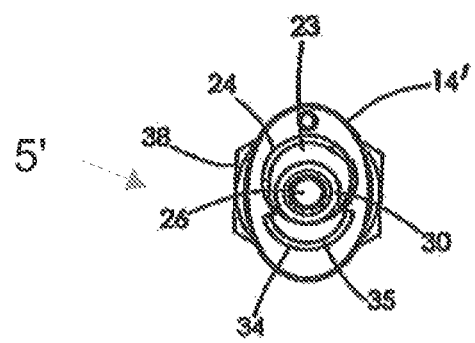
FIG. 5C is an end view of the fixation assembly of FIG. 5A.

Referring now to FIGS. 4A-4C and 5A-5C, another embodiment of fixation assembly 5' is illustrated. This embodiment is very similar to the above-described embodiment, and thus, only the differences will be described herein. In this embodiment, fixation assembly 5' includes a connection assembly 12' that is defined by two components. The first component is a neck 12a', which extends proximally from a flange 14'. As illustrated in FIGS. 4A and 4B, neck 12a' may be defined as a threaded shaft and is configured to threadably receive a nut 38, which is the second component of connection assembly 12'. Also, in this embodiment, drive sleeve 33' may include a gripping surface thereon configured to be gripped by a ratcheting tool (not shown) such as a ratchet. Additionally, in this embodiment, flange 14' may define an opening 40 therethrough that is configured to receive an anti-torque tool (not shown) that rotationally fixes flange 14', spine 20, etc., as the cam members 34 rotate relative thereto.

Similar to opening 40, nut 38 is configured to rotationally fix flange 14', spine 20, etc., as the shaft 32' and cam members 34 rotate relative thereto. In use, nut 38 may be threaded upon neck 12a' until a first surface 38a is in contact with flange 14'. A drive or wrenching tool (not shown) can grasp nut 38, rotationally fixing flange 14', spine 20, etc., as the wrenching tool rotates the shaft 32' and the cam members 34.

Figure 7:
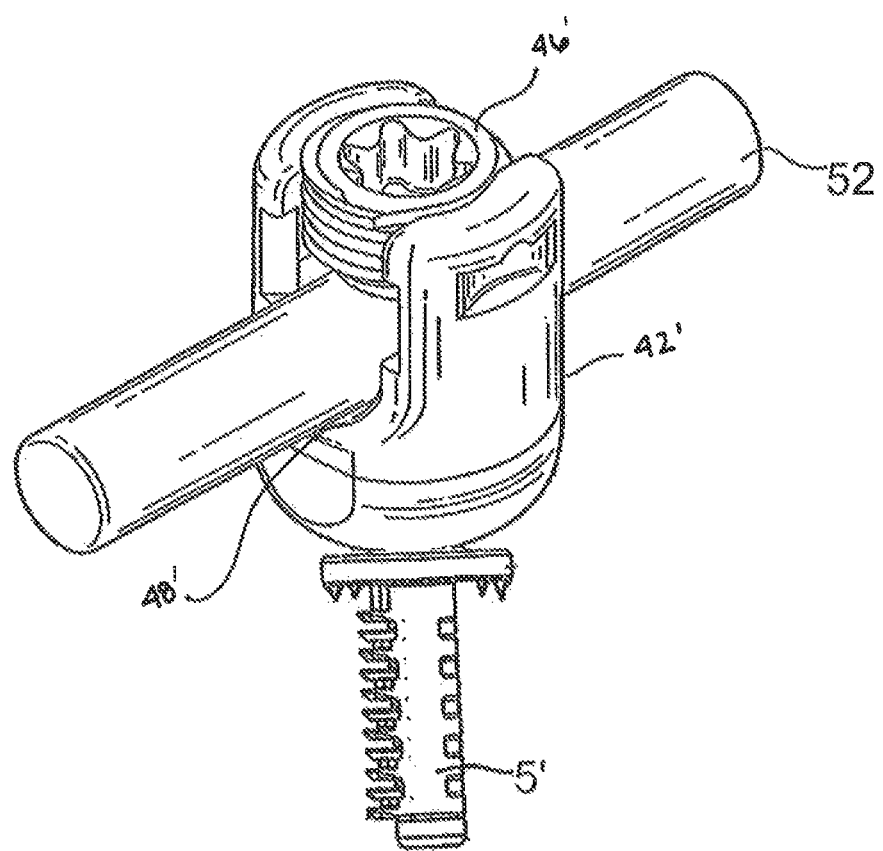
FIG. 7 is an isometric view of a fixation system according to an embodiment of the present disclosure.

The fixation assemblies 5 and 5' can be included as part of a fixation system, for example, as seen in FIGS. 6A, 6B, and 7.

With reference to FIGS. 6A and 6B, a fixation system 1, may include the fixation assembly 5 and a housing assembly 42 coupled to the connection assembly 12 thereof for selectively securing a spinal rod to the osseous tissue. In particular, the housing assembly 42 is coupled to the head 12b (see FIG. 1A) of the connection assembly 12 via the pin 44 such that housing assembly 42 is polyaxially movable about the head 12b of fixation assembly 5. Briefly, the taper lock arrangement of housing assembly 42 generally includes an outer housing 46 that is slidably movable about an inner collet 48 to selectively secure a spinal rod 52 within a U-shaped saddle 50 defined therein. Although the housing assembly 42 is shown as a taper lock arrangement in FIGS. 6A and 6B, the housing assembly 42 can have any suitable configuration such as a set screw type arrangement, as shown in FIG. 7.

As seen in FIG. 7, a set screw type arrangement generally includes a housing assembly 42' in which a set screw 46' is threadably received within the housing assembly 42' to secure a spinal rod 52 within a U-shaped saddled 48' defined therein. The housing assembly 42' can be, for example, configured to mount onto fixation assembly 5 or fixation assembly 5'.

For a more detailed description of example taper lock and/or set screw type housing assemblies, reference can be made to U.S. Pat. Nos. 9,393,049 and 8,814,919, the entire disclosures of each of which are incorporated by reference herein.

Figure 8:
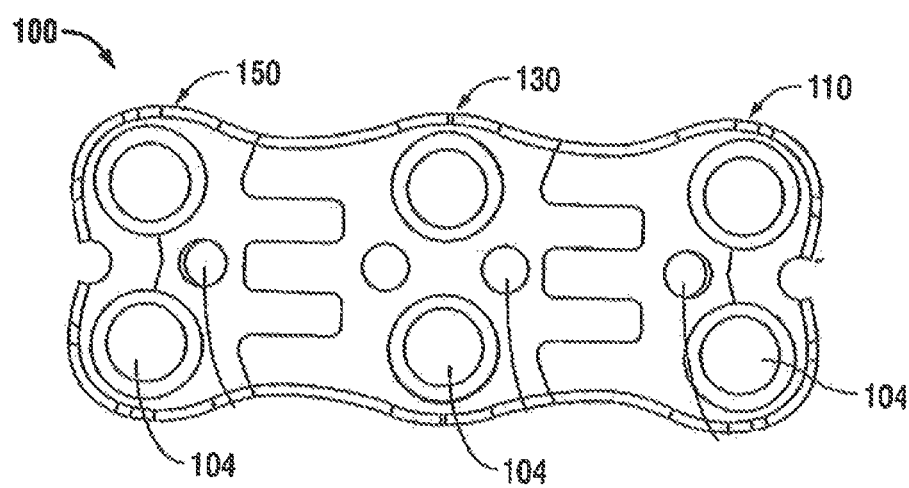
FIG. 8 is a top view of one example of a surgical plate according to the present disclosure.

The presently disclosed fixation systems can, in some embodiments, be included with any suitable spinal plate, for example to secure the spinal plate across one or more vertebrae. For example, as illustrated in FIG. 8, a spinal plate 100 generally define one or more apertures or openings 104 therethrough that receive fixation assemblies, such a bone screws, for securing the spinal plate 100 to vertebrae. The presently disclosed fixation assemblies 5 and 5' may be utilized with, or in place of, such bone screws. Spinal plates such as spinal plate 100 may have two or more sections that are movable relative to one another. For example, spinal plate 100 includes a first end section 110, a middle section 130, and a second end section 150. For a more detailed description of an example spinal plate, reference can be made to commonly owned U.S. Pat. No. 8,636,738, the entire disclosure of which is incorporated by reference herein.

Any of the presently disclosed embodiments, or components thereof, can be formed of any suitable material or combinations of materials such as mixed metallic materials like titanium alloy and cobalt-chromium.

Any of the presently disclosed embodiments, or components thereof can be formed using any suitable technique such as welding, fastening, machining, molding, etc. In some embodiments, one or more of the components can be secured together using any suitable technique such as welding, fastening, machining, molding, etc. Any of the components may be press-fit together.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed:

1. A fixation assembly, comprising:
    a connection assembly; and
    an anchor extending from the connection assembly and defining a longitudinal axis, the connection assembly being concentric about the longitudinal axis, the anchor having:
        a spine that extends along the longitudinal axis, the spine having a first projection and a second projection that extend from the spine in a direction transverse to the longitudinal axis, the anchor defining a slot between the first and second projections;

a cam disposed within the slot of the anchor, the cam positioned to rotate about the longitudinal axis of the anchor between a first position and a second position to enable the first and second projections and the cam to secure the anchor to osseous tissue, the cam aligned with the first and second projections in the first position and misaligned with the first and second projections in the second position; and a shaft rotatably disposed within the anchor and positioned to rotate the cam between the first and second positions, the shaft being rotatable about the longitudinal axis.

2. The fixation assembly of claim 1, wherein the anchor defines an aperture therethrough that receives the shaft.

3. The fixation assembly of claim 2, wherein the cam defines a bore therethrough that receives the shaft therein.

4. The fixation assembly of claim 3, wherein the shaft includes at least one ridge extending longitudinally along the shaft, wherein the bore of the cam is keyed to accommodate the at least one ridge such that the at least one ridge drives rotation of the cam as the shaft rotates about the longitudinal axis of the anchor.

5. The fixation assembly of claim 1, wherein the connection assembly extends proximally from the spine and is configured to support a housing assembly.

6. The fixation assembly of claim 1, further comprising a flange supported on the anchor and configured to limit insertion depth of the anchor.

7. The fixation assembly of claim 1, further comprising a cap that secures the shaft to the anchor.

8. The fixation assembly of claim 1, wherein the connection assembly includes a head section and a neck section, wherein the head section is spherically formed.

9. The fixation assembly of claim 1, wherein the connection assembly includes a threaded neck section configured to threadably receive a nut.

10. The fixation assembly of claim 1, wherein the cam includes an engagement surface configured to cut or thread into osseous tissue.

11. A method for securing a fixation assembly to osseous tissue, the method comprising:

inserting an anchor into a hole in osseous tissue, the anchor defining a longitudinal axis; and rotating a shaft about the longitudinal axis, the shaft being disposed in the anchor relative to the anchor to rotate a cam about the longitudinal axis, the cam being disposed in the anchor from a first position, in which a central axis of the cam is aligned with a central axis of a projection extending from the anchor, the central axis of the cam and the central axis of the projection extending from the longitudinal axis, to a second position, in which the central axis of the cam is misaligned with the central axis of the projection of the anchor to cause the projection and the cam to secure to osseous tissue surrounding the hole.

12. The method of claim 11, wherein rotating the cam from the first position to the second position rotates the cam up to about 180 degrees relative to the anchor.

13. The method of claim 11, further including rotating a plurality of cams disposed in the anchor from a first position, in which each cam of the plurality of cams is aligned with the projection extending from the anchor, to a second position, in which each cam of the plurality of cams is misaligned with the projection of the anchor to cause the projection and the plurality of cams to secure to osseous tissue surrounding the hole.

14. The method of claim 11, further including connecting a spinal rod to a housing assembly supported on a connection assembly of the anchor.

15. The method of claim 11, further including drilling the hole in osseous tissue.

16. A fixation system, comprising:

a housing assembly;

an anchor received within the housing assembly, the anchor defining a longitudinal axis and including a spine that extends along the longitudinal axis, the spine having a first projection and a second projection that extend from the spine in a direction transverse to the longitudinal axis, the anchor defining a slot between the first and second projections; and a cam received within the slot of the anchor, the cam positioned to rotate about the longitudinal axis of the anchor between a first position and a second position to enable the first and second projections and the cam to secure the anchor to osseous tissue, the cam aligned with the first and second projections in the first position and misaligned with the first and second projections in the second position; and a shaft rotatably received within the anchor, and positioned to rotate the cam between the first and second positions, the shaft being rotatable about the longitudinal axis, the shaft separable from, and received within, the cam.

17. The fixation system of claim 16, wherein the anchor includes a connection assembly that extends proximally from the spine and supports the housing assembly thereon.

18. The fixation system of claim 17, wherein the housing assembly is polyaxially mounted on a head of the connection assembly.

19. The fixation system of claim 18, wherein the housing assembly has a taper lock arrangement.

20. The fixation system of claim of claim 16, wherein the housing assembly has a set screw type arrangement.

* * * * *